United States Patent [19]

Wessel et al.

[11] 4,172,432
[45] Oct. 30, 1979

[54] OXYGEN SENSOR MONITOR APPARATUS

[75] Inventors: Wolf Wessel, Oberriexingen; Hermann Eisele, Vaihingen-Enz; Andreas Boehringer, Stuttgart, all of Fed. Rep. of Germany

[73] Assignee: Robert Bosch GmbH, Stuttgart, Fed. Rep. of Germany

[21] Appl. No.: 866,875

[22] Filed: Jan. 4, 1978

[30] Foreign Application Priority Data

Jan. 8, 1977 [DE] Fed. Rep. of Germany ....... 2700629

[51] Int. Cl.² ........................... F02M 7/00; F02B 3/00
[52] U.S. Cl. ........................ 123/32 EE; 123/119 EC; 60/276; 60/285
[58] Field of Search ................... 123/119 EC, 32 EE; 60/276, 285; 73/23; 204/195 S

[56] References Cited

U.S. PATENT DOCUMENTS

| | | | |
|---|---|---|---|
| 2,355,090 | 8/1944 | Love | 123/32 EE |
| 3,841,283 | 10/1974 | Wood | 123/119 EC |
| 4,030,462 | 6/1977 | Sasayama | 123/32 EE |
| 4,040,408 | 8/1977 | Kraus | 123/32 EE |
| 4,120,269 | 10/1978 | Fujishiro | 123/32 EE |

*Primary Examiner*—Ronald B. Cox
*Attorney, Agent, or Firm*—Edwin E. Greigg

[57] ABSTRACT

For use in association with a fuel mixture preparation system of an internal combustion engine which uses closed-loop control based on exhaust chemistry as determined by an oxygen sensor, there is described a circuit which monitors the operational readiness of the oxygen sensor on the basis of its internal resistance. The measurement takes place in a bridge circuit which is supplied with current whenever the sensor is non-operative but which becomes inactive when the sensor is at normal temperatures. The bridge voltages are fed to a comparator which generates an average output value when the oxygen sensor is not yet ready for operation and this average signal is processed in an integrator for final control of the fuel-air mixture.

12 Claims, 1 Drawing Figure

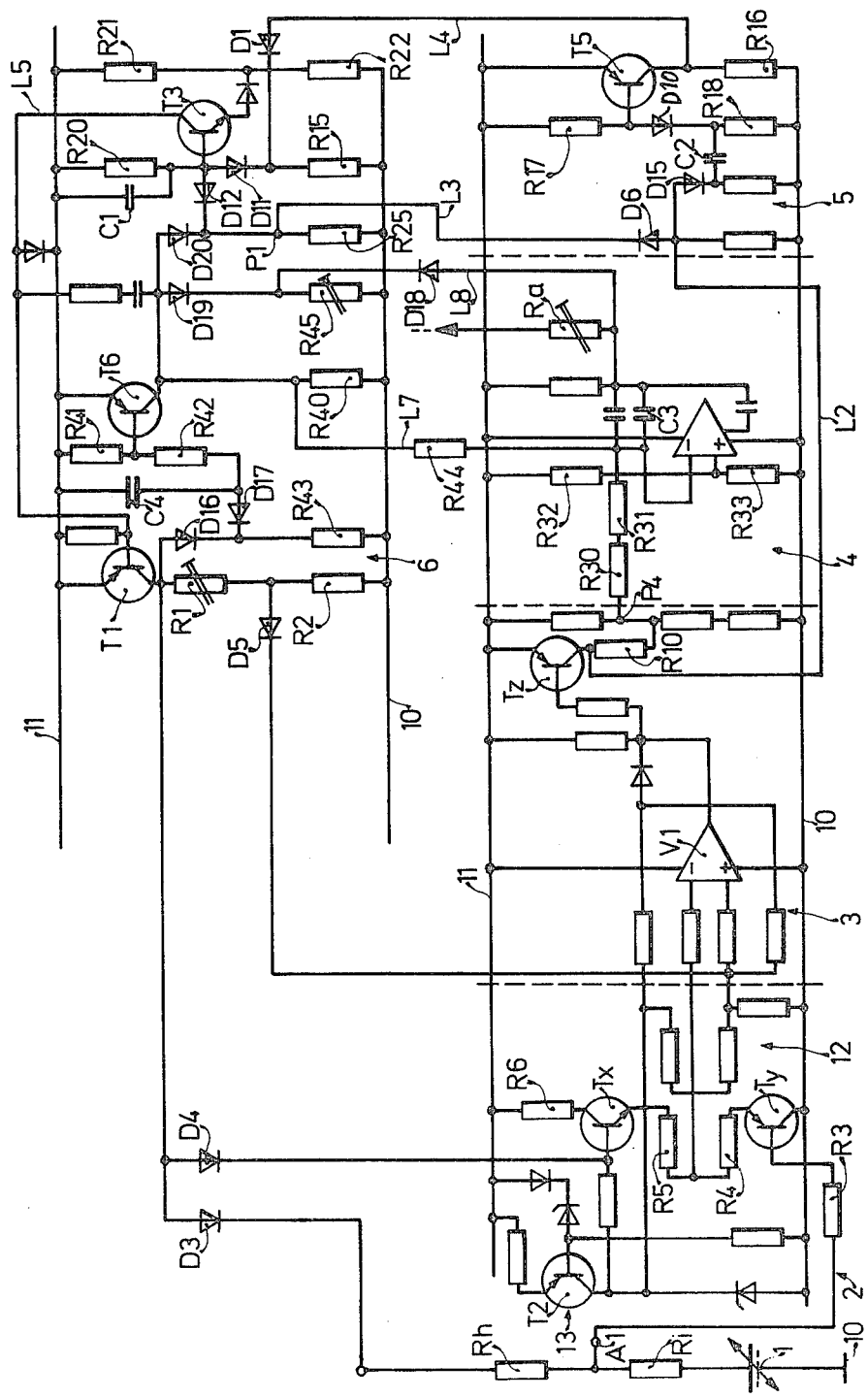

OXYGEN SENSOR MONITOR APPARATUS

BACKGROUND OF THE INVENTION

The invention relates to the fuel mixture control for internal combustion engines. More particularly, the invention relates to a fuel mixture control system which includes an oxygen sensor for monitoring the composition of the exhaust gas and for generating a signal which is used to control the fuel-air ratio in the combustible mixture fed to the engine. In known fuel supply systems of this kind, there may be provided for example a carburetor or an electrical fuel injection system which is subject to regulation by the signals from a so-called λ or oxygen sensor disposed in the exhaust manifold. The λ-sensor signal is processed in appropriate electrical circuitry to produce a control signal which is useable by the fuel injection system or more generally by the fuel preparation system. In commonly used oxygen sensors, the output signal is a step function which changes its value abruptly at the point where the mixture is approximately stoichiometric. However, it is well known that the output signals from the oxygen sensors are not useable in the domain of relatively low temperature, in particular the normal temperature of a cold, i.e. stopped engine. Thus it is generally required to control the engine in some other way until it has reached a suitable elevated temperature at which time the λ-sensor signal is used. The reason for the diminished utility of the λ-sensor signal is the very high internal resistance of the sensor at lower temperatures. Furthermore, in the critical temperature region where the internal resistance of the sensor is high, the output signal is also highly non-linear and for these reasons it is generally preferred in known systems to switch the mixture control to a forward open-loop manner of control and to close the control loop only after the λ-sensor generates clear and useable output signals.

OBJECT AND SUMMARY OF THE INVENTION

It is thus a principal object of the present invention to provide a method and an apparatus for recognizing when the λ-sensor is inoperative and incapable of supplying a useable output signal. It is a further object of the invention to provide a method and an apparatus for switching the mixture control system to open-loop forward control whenever the λ-sensor signal is found to be unuseable for control purposes.

These and other objects are attained by providing an electronic bridge circuit of which the sensor is a part, as well as a monitor circuit connected to the bridge circuit for supplying the latter with current when the sensor is inoperative. The invention further provides a timing circuit which inhibits the function of the monitor circuit when the sensor is found to be operative. It is yet another object of the invention to detect the operational readiness of the λ-sensor by measuring its internal resistance. Still another object of the invention is to associate a comparison resistor with the λ-sensor to make it possible to manufacture the sensor together with a comparison resistor and permit the same to be exchanged together.

A related object of the invention is to optimize the λ-control process for mixture control and to prevent erratic engine operation when the λ-sensor is cold.

The invention will be better understood as well as further objects and advantages thereof become more apparent from the ensuing detailed description of an exemplary embodiment taken in conjunction with the drawing.

BRIEF DESCRIPTION OF THE DRAWING

The single FIGURE of the drawing is a detailed schematic diagram of the invention as part of a known fuel mixture control system shown partially.

DESCRIPTION OF THE PREFERRED EMBODIMENT

Turning now to the single FIGURE of the drawing, there is shown a circuit diagram of an exemplary embodiment of the invention consisting of several major circuit groups whose purpose it is to recognize when the λ-sensor located in the exhaust system delivers a useable signal and in such case to process the signal for mixture control. Conversely, the circuit recognizes when the sensor signal is not useable and in that case engages a monitor circuit so that an average value of the λ-sensor signal is used in the transition from closed to open-loop control. The circuit shown in the drawing illustrates a λ-sensor 1 with an associated internal resistance Ri. The output A1 of the λ-sensor is fed to an impedance converter 2 which makes the λ-sensor signal load resistant and is further passed to a comparator circuit 3 which might be referred to as a λ-switch. The output signal of the comparator circuit 3 controls an integrator 4 whose output is a gradually increasing or decreasing voltage depending on whether the λ-sensor signal is high or low. The output voltage of the integrator 4 is intended to be used by a processing system in order to ultimately prepare a fuel mixture control signal, for example via a resistor Ra. The subsequent processing system (not shown) is a known mixture preparation system for providing a combustible fuel-air mixture for an internal combustion engine. Such a system may be a carburetor or a fuel injection system, preferably operating at least partly electrically. The mixture preparation system uses the output signal provided by the present circuit, i.e. the signal through the resistor Ra for providing closed-loop control of the mixture ratio. In the closed control loop, the induction tube and the exhaust system represent the controlled portions of the system while the mixture preparation system is the controller. The overall circuitry, of which the present invention is a part, is thus a circuit which receives an actual value of the control variable, namely the λ-sensor signal and compares it with set-point or nominal values and performs a continuous control process of the mixture in order to minimize the difference between the actual value and the set-point value.

The circuit shown in the FIGURE also includes a timing member 5 which is connected to the output of the comparator 3 or some circuit components associated with the comparator 3 inasmuch as the output of the comparator is an abruptly changing signal which contains information regarding the prevailing output value of the λ-sensor. Finally, the circuit shown also includes the monitor circuit 6 which receives signals from the comparator 3 and from the timing circuit 5 and which engages the circuit in various places as will be discussed below.

In the following description, individual and special elements, for example the impedance converter 2, the λ switch 3 and the integrator 4 will not be discussed in detail because their exact construction and function is not essential to the present invention or they are known circuits and any description of such circuits will be limited to that required for a comprehension and practicing of the present invention.

The λ-sensor, i.e. its internal resistance Ri, and a resistor Rh are connected in series and form the first half of a bridge circuit while the second half of the bridge circuit consists of the series connection of a resistor R1 and a resistor R2. One point of each bridge is connected to ground or to the negative voltage supply 10. The supply voltage comes from a transistor T1 which is rendered conducting when the monitor circuit 6 is functioning as will be explained below. The collector of the transistor T1 which provides power to the bridge circuit consisting of elements 1, Ri, Rh, R1 and R2 is connected directly to the second half of the bridge consisting of elements R1 and R2 and is connected to the resistor Rh via a diode D3. It will be appreciated that when the transistor T1 blocks, the only elements still operating will be the λ-sensor whose output A1 is connected to the impedance converter 2 because the anode of the diode D3 is pulled down to near ground via the resistors R1 and R2 and blocks, thereby making the resistor Rh ineffective.

Let it be assumed that the transistor T1 is initially conducting, which will be true if the λ-sensor generates a signal that is found not to be useable for closed-loop control. In such a case, the internal resistance Ri of the λ-sensor will be relatively high and the output voltage at the sensor will also be relatively high due, for example, to the base current supplied by the resistor Ty via the resistor R3. The transistor Ty is a part of a further half bridge connected between the negative line 10 and the positive line 11 and further includes resistors R4 and R5, a transistor Tx and a further resistor R6. The transistor Ty is connected as an emitter-follower and serves as an impedance converter for the λ-output signal. The junction of the resistors R4 and R5 is connected to the inverting input of an operational amplifier V1 which is a part of the comparator circuit 3. The non-inverting input of the operational amplifier V1 receives a stabilized voltage from a voltage divider circuit 12 which in turn receives it from a voltage stabilizing circuit 13 that includes a transistor T2 and a number of Zener diodes. The stabilizing circuit is a standard circuit and will not be discussed in greater detail, its purpose is to supply to the positive input of the comparator 1 a threshold potential which is compared with the output voltage of the λ-sensor. It would also be possible to generate the threshold voltage to be variable, for example during the time in which the λ-sensor is gradually being heated and approaches its normal operating domain.

When the transistor T1 conducts, the base voltage of the transistor Tx is pulled to the positive rail via the diode D4, causing the transistor Tx to conduct so that its emitter voltage is only slightly less than the positive supply voltage from the rail 11. It should be noted at this point that any of the semiconductor elements discussed here could be replaced by elements of opposite polarity with appropriate changes in supply voltage being made. The invention is intended to encompass such changes. The transistor Tx and the resistors R4 and R5 constitute one half of a bridge circuit, the center voltage of which is modified by the transistor Ty in accordance with the output from the λ-sensor. The circuit is embodied to permit tapping off the output voltage of the λ-sensor at the junction of the resistors R4 and R5. The voltage from the λ-sensor at the circuit point A1 is compared with a voltage supplied by the monitoring circuit and formed at the junction of the resistors R1 and R2. The latter voltage is transmitted via the diode D5 and a line L1 to the second positive input of the comparator 1. In this manner, one may determine if the half-bridge voltage generated by the λ-sensor is below a predetermined value generated by the resistors R1 and R2 which would signal the operational readiness of the λ-sensor and would permit using it in a closed-loop control circuit. Alternatively, it will be determined if the whole system must be switched over to open-loop control with an average value for the λ-sensor signal. The resistance values of the resistors used as input resistors for the comparator V1 are substantially different in order that the voltage generated at the half bridge R1, R2 has priority at the input of the comparator whenever the λ-sensor is not operationally useable. If that is the case, and the internal resistance Ri of the λ-sensor is correspondingly high, then the negating input of the comparator V1 will see a higher potential than its non-inverting input so that the output of the comparator V1 will be at the negative supply potential. As a result, the subsequent transistor Tz whose emitter is connected to the positive line 11 will conduct and the positive voltage is transmitted from the collector of the transistor Tz via the line L2 and through the diode D6 to the monitor circuit 6. The output voltage at the collector of the transistor Tz pulls the voltage at a circuit point P4 in the direction of the positive supply until a subsequent integrator starts to integrate in a single direction as will be discussed in greater detail below. The positive voltage at the collector of the transistor Tz travels to the circuit point P1 of the monitor circuit and also activates the timing circuitry 5. The latter is a so-called economy monostable multivibrator consisting of a switching transistor T5 whose emitter is connected to the positive line 11 and whose collector is connected through a resistor R16 to ground. Connected to the base of the transistor T5 is the series connection of a resistor R17, a diode D10 and a further resistor R18. The latter three elements constitute a voltage divider circuit so designed that, when the diode D10 normally conducts, the base voltage of the transistor T5 is sufficiently negative to permit conduction of the transistor T5. The timing circuitry 5 is then in its normal, stable state. However, positive pulses admitted to the diode D15 from the collector of the transistor Tz may reach the base of the transistor T5 via a timing capacitor C2, thereby blocking the diode D10 until the positive potential in the base circuit of the transistor T5 has decayed. If the λ-sensor is operating normally, its output signal will periodically change in the manner of a two-point control system so that the transistor T5 is normally blocked periodically. This short term blockage is sufficient to release the base circuit of a subsequent transistor T3 located within the monitor circuit 6. During a blockage of the transistor T5, the base of the transistor T3 does not receive any control signal via the line L4 because the anode of the diode D1 lies at substantially negative voltage. The capacitor C1 is thus able to charge to negative values via the diode D11 and the resistor R5 and the transistor T3 thus remains blocked for a prolonged period of time. If, on the other hand, the λ-sensor is inoperative so that the positive voltage at the collector of the transistor Tz is maintained for substantial periods of time, then the timing circuitry 5 will return to its stable state and cause the transistor T5 to conduct, thereby blocking the diode D11 connected to the base of the transistor T3. Now the capacitor C1 begins to exchange charge via the resistor R20 until, finally, the transistor T3 receives base current through the resistor R20 and starts to conduct inasmuch as its emitter lies at a fixed potential determined by the resistors R21 and R22. When the transistor T3 conducts, the line L5 carries a negative voltage to the base of the transistor T1, thereby causing it to conduct, assuming that the output voltage from the non-operational λ-sensor is high enough to permit the generation of the required voltage. The positive voltage from the collector of the transistor Tz is also transmitted through the diode D6 and the line L3 to the point P1 in the base circuit of the transistor T3 where it blocks a diode D12 so that the parallel circuit formed by this diode D12 and a parallel resistor R25 remains without current and thus without effect. In this state of the circuit, the apparatus depicted in the FIGURE permits continous monitoring of the λ-sensor to determine its operational state.

As the λ-sensor becomes gradually warmer, its internal resistance Ri falls, so that the voltage drop across the sensor will no longer suffice to hold the comparator V1 in its first switching state. Accordingly, its output goes positive and the subsequent transistor Tz is blocked. This implies an operational readiness of the λ-sensor and signals a time when it may be used for closed-loop control as an additional correcting factor for the fuel-air ratio. Inasmuch as the positive voltage at the collector of the transistor Tz now vanishes, the diode D6 is blocked and the circuit point P1 in the base circuit of the transistor T3 is released so that the transistor T3 blocks practically immediately even if the output of the timing circuitry 5 still supplies positive voltage to the other branch consisting of the diode D11 and the resistor R15, or if the capacitor C1 is negatively charged. The switchover of the transistor T3 also blocks the transistor T1.

From this point on, the circuit operates normally and none of the voltage divider circuits exerts any further influence. The diodes D3, 4 and 5 are all blocked as is a further diode D16 connected to the collector of the transistor T1 because the anodes of all these diodes are placed substantially at ground potential when the transistor T1 conducts. Thus, any influence of the monitor circuit 6 on the processor circuit consisting of the circuits 2, 3 and 4 is terminated. Under normal conditions, the output of the λ-sensor then travels through the unaffected impedance converter 2 to the comparator which changes its output voltage in accordance with the abrupt changes of the λ-sensor output potential and exerts a control on the subsequent integrating circuit.

As a consequence, the voltage at the collector of the transistor Tz will alternate constantly between the two voltage levels and this signal travels from the point P4 through the resistors R30 and R31 to one input of an operational amplifier equipped with an integrating capacitor C3 and serving as an integrator. The other input of this integrator receives a fixed potential from a voltage divider consisting of resistors R32 and R33. The output of the integrator at the resistor Ra thus is the usual and known sawtooth voltage.

It will be appreciated that the monitor circuit 6 should not be turned on every time that the collector of the transistor Tz becomes positive during the periodic back-and-forth shifting of the comparator output signal. Such a periodic turn-on is prevented by the timing circuitry 5 discussed previously and by the subsequent timing member C1/R20 as well as well as through the lines L3 and L4 which permit different methods of actuation via different partial branches of the base voltage divider of the transistor T3. If, during the normal switching behavior of the transistor Tz, its collector returns to positive voltage, the circuit point P1 also receives a positive voltage via the diode D6 and the diode D12 is blocked again but, at the same time, the positive voltage jump triggers the timing circuitry 5 and the capacitor C2 blocks the diode D10, thereby also blocking the transistor T5 and placing the timing circuitry 5 into its metastable state in which the diode D1 is blocked. Therefore, the base branch circuit consisting of the diode D11 and R15 is not affected and the transistor T3 remains blocked at least for the time during which the metastable state of the timing circuitry 5 persists. The time constant of this monostable multivibrator 5 needs to be only large enough to permit the capacitor C1 to be charged to negative voltages so that, during a normal positive voltage pulse at the collector of the transistor Tz, the negative voltage at the base of the transistor T3 from the capacitor C1 will predominate. This is so because as soon as the output voltage from the λ-sensor changes, thereby producing a negative voltage at the collector of the transistor Tz, the circuit junction P1 is definitely released as also is the voltage divider branch D12, R25 permitting the continued blockage of the transistor T3 even if the absence of a timely positive control pulse causes the monostable flop-flop 5 to return from its metastable state to its stable state at a later time so that, when the transistor T5 conducts, the diode D1 may transfer a positive voltage to the base of the transistor T3. Only in case the internal resistance of the λ-sensor is too high, indicating that it is not operationally ready, so that the output voltage of the transistor Tz remains positive for extended periods of time, are both voltage divider branches D12, R25 and D11, R15 supplied with positive voltage via lines L3 and L4, respectively, thereby causing both diodes D12 and D11 to block and permitting base current to flow to the base of the transistor T3 via the resistor R20 and permitting conduction of the transistor T3.

The remaining parts of the circuit serve the exclusive purpose of adjusting the output signal from the integrator 4 in such a way that the subsequent fuel control circuit which is connected behind the processing circuit according to the present invention receives an average signal via the resistor Ra.

The circuit includes a further transistor T6 whose emitter is connected to the positive line 11 and whose collector is connected through a resistor R40 to the more negative supply line (ground). The base of the transistor T6 is connected to a voltage divider circuit consisting of the series connection of resistors R41, R42 and a diode D17 as well as a resistor R43. The junction of the resistors R41 and R42 is connected to the base of the transistor T6 and these resistors are paralleled by a capacitor C4. The collector of the transistor T1 is connected via a diode D16 to the junction of the diode D17 and the resistor R43 so that, when the transistor T1 conducts, it raises the voltage across the resistor R43 until the transistor T6 no longer receives base current and blocks. Therefore, the collector of the transistor T6 goes to a negative voltage and the line L7 transmits to the inverting input of the integrating operational amplifier a negative voltage causing its output to integrate in the positive direction. The output of the integrator is then pulled down toward negative values by a line L8 so as to provide the desired average value for λ in the open-loop control phase of the system. The output of the integrator 4 is connected via a diode D18 to an adjustable resistor R45 the other end of which is connected to the negative supply line and whose junction with the diode D18 is connected to a further diode D19 that is coupled to the collector of the transistor T6. When the system is being operated in open-loop control, i.e. when the transistor T1 conducts, the transistor T6 blocks and permits the modification of the output voltage from the integrator 4.

Viewed in summary, the apparatus according to the invention is a circuit which permits the measurement of the magnitude of the internal resistance of the oxygen sensor (λ-sensor) and thus to recognize the operational readiness of the sensor. The circuit is so designed that when the λ-sensor is cold, it is connected in a half-bridge circuit with a comparison resistor and the center voltage of this half bridge is compared with the center voltage of a second half bridge which is fixed and derived from the ratio of the resistors R1 and R2. If the internal resistance of the sensor is sufficiently small, corresponding to an elevated temperature, the voltage in the part of the bridge containing the sensor will be smaller than the comparison voltage and the system will switch over to closed-loop control which, furthermore, causes the entire bridge circuit to become ineffective. By choosing the appropriate value of the resistor R1, it is possible to adjust the system to switch over from closed-loop to open-loop control for any desired value of the internal resistance of the λ-sensor. It is a particular advantage of the present invention that the comparison resistor Rh which is connected with the sensor in the half bridge circuit may be connected to it at the time of manufacture. This is particularly advantageous because the internal resistance of any particular sensor depends on its manner of manufacture and, by combining the sensor with its own comparison resistor at the time of fabrication, a sensor and its comparison resistor may be exchanged together while no changes need be made in the remaining processor circuit.

It has been mentioned that the voltage divider circuit connected to the base of the transistor T3 includes a resistor R20 with a parallel capacitor C1 which together form an RC element that introduces a time delay into the behavior of the potentials in the base circuit of the transistor T3. If it is assumed that the diode D11 or the diode D3 had been conducting, permitting the capacitor C1 to be charged to an appropriately negative potential, this potential will be maintained during the subsequent simultaneous blockage of the diodes D11 and D12 and is only slowly reduced via the relatively high valued resistor R20. During this entire time, the transistor T3 will be blocked even if the time constant of the timing member 5 has been exceeded and the diode D11 is blocked by the positive potential present at the diode D1 when the transistor T5 conducts. Thus it is possible to set the amount of time elapsing prior to the onset of conduction of the transistor T3 by appropriate choice of the dimensions of the RC elements C1, R20.

Finally, it is possible to connect the junction of the diode D12 and the resistor R25, i.e. the circuit point P1, with the collector of the transistor T6 via a diode D20. If this is done, the diode D12 will be blocked when the transistor T6 conducts and the transmission T1 and T3 are both blocked.

Under those conditions, the following function takes place: When the λ-sensor is not ready for operation, transistors T1 and T3 conduct and transistor T6 is blocked. Normally, the point P1 would be at negative voltage via resistor R25 and would block the transistor T3 via the diode D12. However, for the case of sensor monitoring in which T3 is intended to conduct, the transistor Tz will conduct and can pull the circuit point P1 to positive values via the diode D6, thereby permitting the transistor T3 to continue conduction. At the first instance of operational readiness of the sensor, the transistor Tz will block. Therefore the point P1 goes to negative values and C1 can change toward negative values via resistor R25, while the transistor T3 will block. Thus the transistor T1 also blocks, and eventually causes the transistor T6 to conduct after a delay defined by the magnitude of the capacitor C4 and the resistor R42, thus pulling the circuit point P1 back to the positive values. The delay induced by the combination C4/R42 must be long enough to permit a definite negative charge to be acquired by the capacitor C1 through the resistor R25. Once this first charging of C1, which was made possible by the delayed switching of the transistor T6, has taken place, it is thereafter without effect for any regular alternation of the λ-sensor potential, because T6 remains in conduction and P1 remains at positive voltage. Any further charging of the capacitor C1 can take place only by pulses from the monostable flip-flop 5 which must be sufficiently long to permit C1 to exchange charge toward negative voltages. The time constant defined by C1 and R20 must be large enough so that T3 is definitely blocked in-between two pulses from the monostable flip-flop 5. The time elapsing between pulses of the monostable flip-flop 5 is defined by the inherent control loop actuation frequency.

The foregoing relates to preferred exemplary embodiments of the invention, it being understood that other embodiments and variants thereof are possible within the spirit and scope of the invention.

What is claimed and desired to be secured by Letters Patent of the United States is:

1. An apparatus for monitoring the operational readiness of an oxygen sensor, said oxygen sensor being part of a fuel mixture preparation system for an internal combustion engine, and wherein the improvement comprises:

that said oxygen sensor is connected in a bridge circuit containing resistors, and said apparatus includes a monitor circuit connected to said bridge circuit for supplying current to said bridge circuit when said oxygen sensor is inoperative, and still further comprises a timing circuit which inhibits the action of said monitor circuit when the oxygen sensor is in normal operative condition.

2. An apparatus as defined by claim 1, further comprising an electrical comparator connected to said oxygen sensor, for generating output signals in synchronism with the output signals of an operative oxygen sensor, there being connected behind said comparator an integrator to generate a fuel control signal, the output from said comparator being further supplied to a monostable multivibrator acting as a timing circuit and the output of said multivibrator being connected to a second timing member (C1, R20) for inhibiting the effect of said monitor circuit.

3. An apparatus as defined by claim 1, wherein said oxygen sensor is connected in series with a comparison resistor (Rh), thereby forming the first half of a circuit bridge, and there being connected in parallel with said first half bridge a second half bridge (R1, R2) for generating a fixed voltage, and wherein the voltages of both halves of said half bridges are coupled to respective inputs of said comparator; whereby, when said oxygen sensor is inoperative, said comparator generates a constant and unvarying output potential.

4. An apparatus as defined by claim 3, wherein both of said half bridges are supplied with current by a switching transistor (T1) controlled by said timing circuit.

5. An apparatus as defined by claim 4, wherein said switching transistor (T1) is controlled by a second switching transistor (T3) the base of which is connected to a voltage divider circuit consisting of resistors, capacitors and diodes, whereby said transistor (T3) may be directly controlled by said comparator and by a further transistor (Tz) and by said timing circuit.

6. An apparatus as defined by claim 5, wherein said voltage divider circuit connected to the base of said transistor (T3) includes two branches connected to ground, the first of said branches including a diode (D11) and a resistor (R15) and the second of said branches including a diode (D12) and a resistor (R25), and wherein the junctions of said diodes with their respective resistors are connected to the output of said comparator directly or via said timing circuit.

7. An apparatus as defined by claim 6, wherein there is connected to the base of said transistor (T3) a second timing member (C1, R20) whereby said transistor (T3) can be rendered conducting only after the expiration of a finite time interval.

8. An apparatus as defined by claim 7, including means for blocking said diodes (D12, D11) connected to the base of said transistor (T3); whereby when said diodes (D12, D11) are simultaneously blocked, and the time constant of said second timing member (R20,C1) has expired, said transistor (T3) conducts and causes said transistor (T1) to supply the half bridge circuits with supply current.

9. An apparatus as defined by claim 8, wherein said timing circuit is a monostable multivibrator (C2, T5) whose stable state is the state in which the transistor (T5) conducts and receives no base signal and supplies a positive voltage to said diode (D11) to block the same.

10. An apparatus as defined by claim 9, wherein said transistor (Tz) connected to the output of said comparator is coupled via a diode (D6) to the junction of the diode (D12) and the resistor (R25); whereby said diode (D12) is blocked as soon as a control voltage corresponding to a high internal sensor resistance is present.

11. An apparatus as defined by claim 10, further comprising a transistor (T6) controlled by said current producing transistor (T1), said transistor (T6) being blocked when said transistor (T1) conducts and the collector of said transistor (T6) being connected to both the input and the output of said integrator; whereby there is provided by said integrator an average output control value in open-loop operation of said fuel control system.

12. An apparatus as defined by claim 11, wherein the junction of said diode (D12) and said resistor (R25) is connected via a further diode (D20) to the collector of said transistor (T6); whereby when said oxygen sensor operates properly and said transistor (T6) conducts, the status of said monitor circuit is determined exclusively by the control of said second timing member (C1, R20) as initiated by said timing circuit.

* * * * *